United States Patent [19]

Blackford et al.

[11] Patent Number: 5,374,396
[45] Date of Patent: Dec. 20, 1994

[54] SYRINGE INJECTION SYSTEM FOR MEASURING NON-VOLATILE RESIDUE IN SOLVENTS

[75] Inventors: David B. Blackford, St. Paul; Thomas A. Kerrick, Forrest Lake, both of Minn.; David S. Ensor, Chapel Hill; Elizabeth A. Hill, Durham, both of N.C.

[73] Assignee: TSI Incorporated, St. Paul, Minn.

[21] Appl. No.: 878,740

[22] Filed: May 5, 1992

[51] Int. Cl.$^5$ ............................................. G01N 15/12
[52] U.S. Cl. .................................... 422/73; 422/110; 422/103; 436/36; 436/164; 356/37; 356/335; 356/336; 356/337; 137/876
[58] Field of Search ............... 422/73, 110, 112, 115; 436/36, 164, 181; 137/896, 897; 366/101; 356/37, 335, 336, 337

[56] References Cited

U.S. PATENT DOCUMENTS

| 2,645,463 | 2/1949 | Stearns | 137/896 |
|---|---|---|---|
| 3,726,297 | 4/1973 | Heimann et al. | 137/896 |
| 3,900,290 | 8/1975 | Hornstra | 422/73 |
| 4,025,307 | 5/1977 | Randolph et al. | 422/73 |
| 4,164,960 | 8/1979 | Howard | 137/897 |
| 4,405,087 | 9/1983 | Mata-Garza | 366/173 |
| 4,586,825 | 5/1986 | Hayatdavoudi | 366/137 |
| 4,729,876 | 3/1988 | Hennessy et al. | 422/103 |
| 4,761,074 | 8/1988 | Kohsaka et al. | 356/37 |
| 4,790,650 | 12/1988 | Keady | 356/37 |
| 4,794,086 | 12/1988 | Kasper et al. | 436/36 |
| 5,059,395 | 10/1991 | Brittenham et al. | 422/73 |
| 5,098,657 | 3/1992 | Blackford et al. | 422/73 |
| 5,178,836 | 1/1993 | Kitamori et al. | 422/73 |

FOREIGN PATENT DOCUMENTS

| 8802116 | 3/1988 | European Pat. Off. | 422/73 |
|---|---|---|---|
| 9007259 | 7/1990 | European Pat. Off. | 422/73 |

Primary Examiner—Robert J. Warden
Assistant Examiner—Hien Tran
Attorney, Agent, or Firm—Frederick W. Niebuhr

[57] ABSTRACT

The concentration of non-volatile residue in a test solvent is determined by generating multiple liquid droplets from a liquid stream including the solvent and ultrapure water. The droplets are dried to form a stream of multiple particles of the non-volatile residue. A supply of ultrapure deionized water is caused to flow continuously toward a non-volatile residue monitor, at a constant fluid flow rate. Upstream of the residue monitor, a syringe is provided for intermittently injecting a test solvent into the fluid stream. In one case, the solvent is injected for several minutes at a constant flow rate substantially less than that of the ultrapure water. A mixing valve, downstream of the point of solvent introduction, causes turbulent flow to thoroughly mix the solvent and water. In an alternative approach, a syringe is used to instantaneously inject solvent in the form of bursts. In this case, flow is laminar rather than turbulent, to maintain the solvent burst separate from the water, while it flows with the water in the fluid stream. In either case, the composite of liquid and solvent is provided to the residue monitor. The monitor output is a particle count. A microprocessor receives the particle count and converts the count to derive values for non-volatile residue concentration in the solvent.

28 Claims, 3 Drawing Sheets

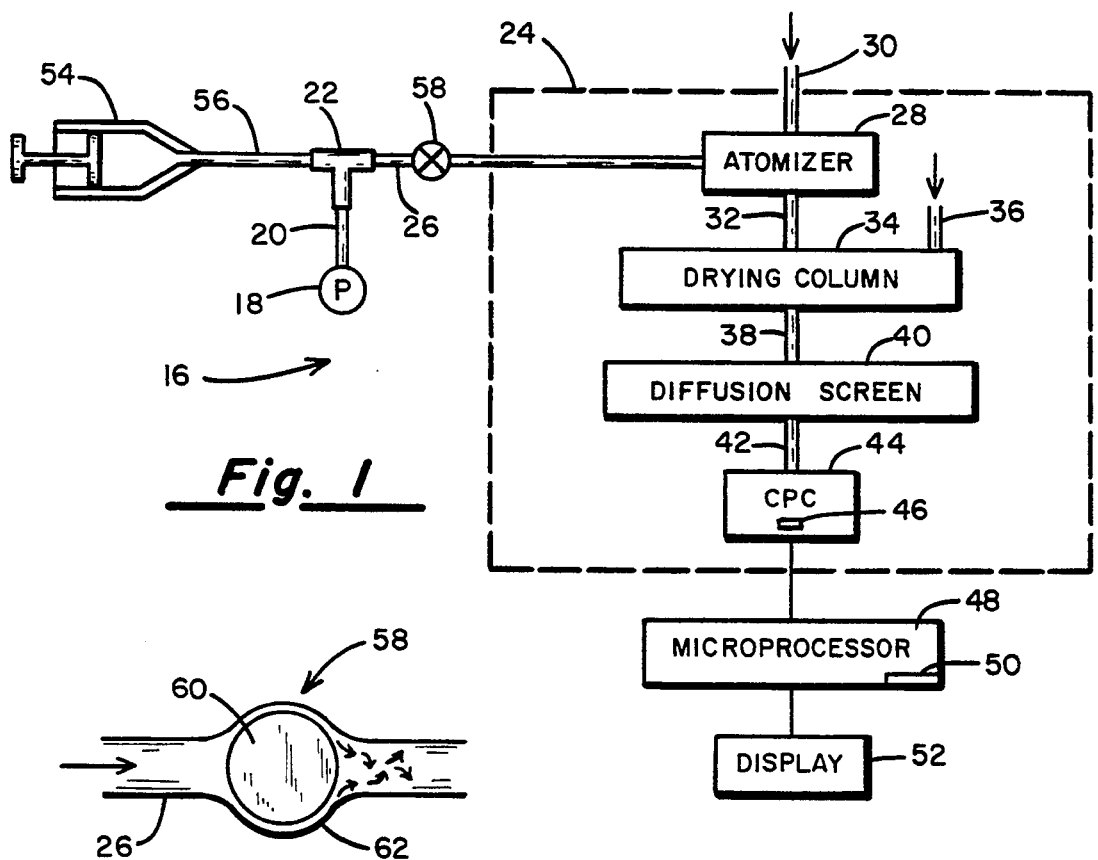
*Fig. 1*
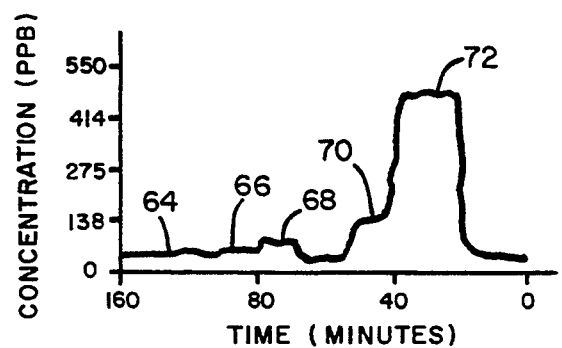
*Fig. 3*
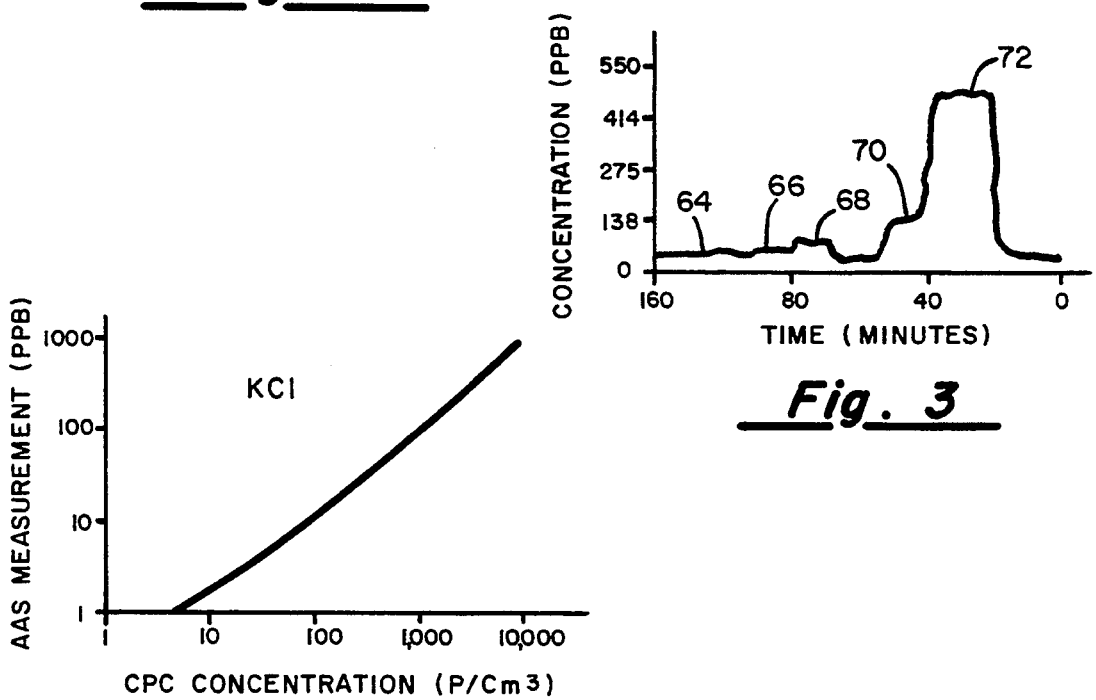
*Fig. 2*
*Fig. 4*

SYRINGE INJECTION SYSTEM FOR MEASURING NON-VOLATILE RESIDUE IN SOLVENTS

BACKGROUND OF THE INVENTION

This invention relates to the measurement of concentrations of non-volatile residue in liquids, and more particularly to systems and processes for determining non-volatile residue concentrations in solvents.

It is known that the fabrication of very large scale integrated (VLSI) circuits requires an abundance of ultrapure water. More particularly, a complete fabrication process may involve over fifty stages of processing the surface of the semiconductor wafer. A washing with the ultrapure water follows each stage of processing, for removal of chemicals used in that stage. Accordingly, thousands of liters of ultrapure water may be used in processing a single wafer. Any non-volatile residue present in the ultrapure water can remain on the surface of the wafer after the water has evaporated, possibly causing defects in the resulting semiconductor device. This gives rise to a need to monitor the ultrapure water for the presence of non-volatile residue, to insure that the concentration of such residue remains at or below an acceptable level.

Similarly, there is a need to determine the non-volatile residue concentration in various solvents used in etching, deposition, cleaning and other stages of fabrication. Herein, "solvents" is used generically to include organic solvents such as isopropyl alcohol and acetone, and inorganic solvents such as hydrochloric acid, hydrofluoric acid, ammonium hydroxide, hydrogen peroxide and water. These solvents must be tested to determine their purity. Further, as to solvents used in cleaning, it is advantageous to measure residual contamination extracted from components that have been cleaned in the solvent, as an indication of the degree to which such components have been cleaned, and as an indication of whether the solvent remains suitable for cleaning further components.

Systems have been developed and employed successfully in continuously monitoring the quality of ultrapure water. For example, U.S. Pat. No. 5,098,657 (Blackford et al) discloses an apparatus for measuring non-volatile residue concentrations in ultrapure water. Fixed and adjustable flow restrictive elements are arranged to provide a constant, pressure controlled flow of the water to an atomizer. At the atomizer the water is formed into droplets which are later dried to provide non-volatile residue particles. An electrostatic aerosol detector determines the particle concentration, which provides an indication of the purity of the water.

Solvents, however, do not lend themselves to this type of continuous flow system, in which the fluid flows at a rate of at least fifty milliliters per minute. Due in part to their volatility, and in the case of acids their corrosiveness, solvents give rise to safety concerns in their handling, release vapor emissions, and create waste disposal problems. Accordingly, solvents preferably are used and tested in the lowest workable amounts and concentrations.

The conventional method for testing solvents for non-volatile residue is to evaporate a measured quantity of the solvent in a previously weighed container. The original volume of liquid and the weight of material remaining after evaporation, are used to compute residue concentration. Given the need to determine residue concentrations in the single part per billion range, a relatively high volume of the solvent (e.g. one liter) is required for an accurate measure of concentration. The testing procedure is time consuming in view of the need to completely evaporate the solvent. This approach is costly, yet can not provide real time residue concentration data. Such testing gives rise to difficulties in solvent handling, potentially harmful vapor emissions, and waste disposal problems.

While the above discussed needs and difficulties in ascertaining solvent purity are perhaps particularly apparent in connection with fabrication of semiconductor devices, they arise in other industries, e.g. manufacture of disk drives and recording media, precision optics, inertial guidance and aerospace applications.

Therefore it is an object of the present invention to provide a system and process for accurately determining levels of impurities in solvents by testing extremely small quantities of the solvents.

Another object of the invention is to provide a simple and rapid means for obtaining real time information on the concentration of non-volatile residues in volatile solvents.

A further object is to provide a low cost approach to monitoring contamination levels of cleaning solvents used in semiconductor wafer processing and other manufacturing techniques that require exceptionally clean parts.

Yet another object is to provide a process for testing contamination levels in solvents employed during various stages of semiconductor wafer processing (and other processes), with equipment already utilized in monitoring contamination levels in ultrapure water.

SUMMARY OF THE INVENTION

To achieve these and other objects, there is provided an apparatus for measuring the concentration of non-volatile residue in a test liquid. The apparatus includes a droplet forming means for receiving a fluid stream and for using at least a portion of the fluid stream to generate multiple liquid droplets. A drying means is disposed downstream of the droplet forming means, for causing evaporation of the liquid droplets to form a particle stream of multiple, substantially non-volatile particles. A particle counting means, disposed downstream of the drying means, receives the particle stream. The particle counting means includes a viewing region, and generates a particle count of the number of the non-volatile residue particles passing through the viewing region. A first fluid supply means is coupled to the droplet forming means. The first fluid supply means provides a fluid stream comprised of a carrier liquid moving at a substantially constant first flow rate. A second fluid supply means is in fluid communication with the first fluid supply means. The second fluid supply means controllably and intermittently introduces a test liquid into the fluid stream at a point upstream of the droplet forming means.

In one preferred form of the invention, the second fluid supply means is a motorized syringe injector that introduces the test liquid, e.g. a solvent, at a substantially constant flow rate less than one percent of the flow rate of the carrier liquid, ultrapure water. More preferably, the ultrapure water flow rate is at least 50 milliliters per minute, while the solvent flow rate is about 0.03 milliliters per minute. A mixing valve, at the point of solvent introduction or just downstream, causes a turbulent flow to insure a thorough mixing of the solvent and ultrapure water.

In another preferred approach, the solvent is introduced to the ultrapure water substantially instantaneously. In contrast to the first approach, the solvent must be injected in a non-turbulent manner, to form plugs of the solvent that flow in the fluid stream with the ultrapure water, yet remain separate and distinct from the water. The individual plugs can be extremely small in volume, e.g. in the 100 microliter range or less.

Thus, neither approach requires large amounts of the solvent being tested. As a result, problems associated with volatile solvents, such as undesirable emissions to the atmosphere, waste disposal difficulties, and safety concerns in handling, are kept to a minimum. In the plug injection approach, this is due to the small amount, per se. In the turbulent mixture approach, this is due to the dramatic dilution of the solvent.

The introduction of the solvent in plugs affords several further advantages. First, this approach is simpler and requires less skill, since there is no need to maintain a constant or steady solvent injection rate. No mixing valve or other means to generate a turbulent flow is required, since there is no need to form a mixture of the solvent and the ultrapure water. Results are obtained more rapidly, based upon the direct response of the particle counter in detecting non-volatile residue particles corresponding to the plug of solvent. By contrast, the mixture approach requires more time, e.g. several minutes, to stabilize the solvent/water mixture and maintain its stability.

With either approach, however, concentrations can be determined by counting residue particles with known and available equipment. The droplet forming means preferably is an atomizer, but also can be a nebulizer or a vibrating orifice droplet generator. The preferred counting means include a condensation particle counter and a diffusion filter upstream of the CPC for removing ultrafine particles before the particle stream reaches the CPC. Alternatively, a light scattering particle spectrometer, an aerodynamic particle sizer or an electrostatic aerosol detector may be employed in counting the non-volatile residue particles.

A further aspect of the present invention is a process for determining the concentration of non-volatile residue in a test liquid. The process includes the following steps:

moving a carrier liquid in a fluid stream at a substantially constant first flow rate;
controllably and intermittently introducing a test liquid into the fluid stream;
downstream of a point at which the test liquid is introduced, generating multiple liquid droplets comprised of at least a portion of the fluid stream;
drying the liquid droplets to form a particle stream of multiple substantially non-volatile residue particles;
counting the non-volatile residue particles to obtain a particle count; and
deriving the concentration of non-volatile residue in the test liquid, based upon the particle count.

The test liquid may be introduced at a constant flow rate, with the flow rate preferably being at most one percent, and more preferably at most 0.1 percent, of the carrier liquid flow rate. The test liquid should be miscible in the carrier liquid. When this method is employed, the particle counting step includes obtaining a background count corresponding to a fluid stream including just the carrier fluid, and obtaining a composite count corresponding to both the test liquid and carrier liquid in the fluid stream. The derivation step includes subtracting the background count from the composite count.

Alternatively, the test liquid may be introduced substantially instantaneously, in a non-turbulent manner. This forms plugs of the test liquid that flow in the fluid stream with the carrier liquid, yet remain separate and distinct. Experimentation has shown that with this approach, as well, there is a need to subtract a background count.

Thus, in accordance with the present invention, a system for monitoring the contamination levels in ultrapure water, further is useful (with appropriate modifications as described) in determining the contaminate levels in solvents. A solvent can be introduced to form discrete plugs flowing in the fluid stream, or as part of a solvent/water mixture. In either event, the system is simple and reliable, affording highly accurate readings without requiring the excessive amounts of solvent used in the conventional approach of determining residue concentrations by evaporation. Tests can be performed rapidly, especially when the solvent is introduced as a plug, enabling repeated testing to verify results, or timely adjustments in response to sensing undesirably high residue concentrations.

BRIEF DESCRIPTION OF THE DRAWINGS

For a further understanding of the above and other features and advantages, reference is made to the following detailed description and to the drawings, in which:

FIG. 1 is a schematic view of a system for determining non-volatile residue concentrations, constructed in accordance with the present invention;

FIG. 2 is a schematic view of a mixing valve employed in the system of FIG. 1;

FIG. 3 is a chart illustrating non-volatile residue concentration data, taken over a predetermined time of operating the system of FIG. 1;

FIG. 4 is a conversion chart relating parts per billion to particle count per cm$^3$;

DETAILED DESCRIPTION OF THE PREFERRED EMBODIMENTS

Figure 5:
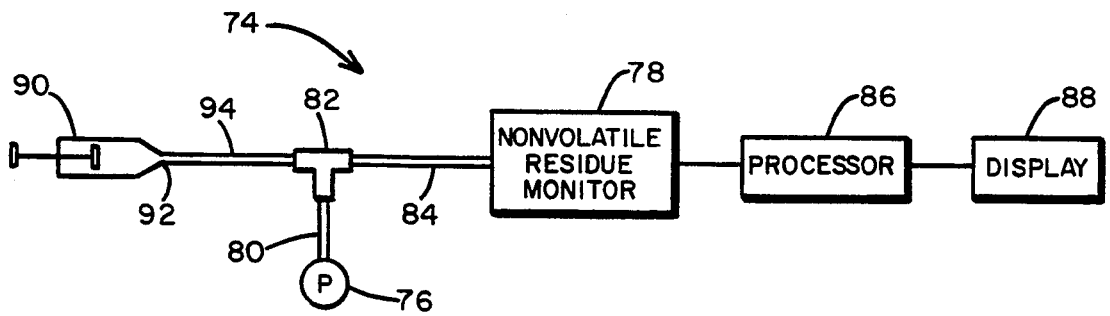
FIG. 5 is a schematic view of an alternative non-volatile residue concentration measurement system, constructed in accordance with the present invention.

Turning now to the drawings, there is shown in FIG. 1 a system 16 for determining the concentration of non-volatile residue in a test liquid, e.g. a solvent. The system includes a pump 18 for supplying ultrapure, deionized water through a conduit 20 to a "T" fitting 22, and then to a non-volatile residue monitor 24 via a conduit 26. Through proper control of pump 18 and further equipment not illustrated but known to those skilled in the art, the ultrapure water is supplied at a steady, precisely controlled rate, preferably in the range of about 50 to about 70 ml per minute. A preferred non-volatile residue monitor is available from TSI Incorporated of St. Paul, Minn., and sold under the brand name LIQUI-TRAK.

Residue monitor 24 is used to continuously monitor the concentration of non-volatile residue in the ultrapure water, to insure a level of purity in the water sufficient for its intended use, e.g. in cleaning a wafer between stages of semiconductor device fabrication. A small portion (e.g. about one percent) of the ultrapure water is directed to an atomizer 28 of the monitor. Compressed air or nitrogen also is supplied to the atomizer at a constant flow rate, via a line 30.

The output of atomizer 28 is a stream of droplets of the ultrapure water, which travel through a conduit 32 to a drying column 34. Compressed air or nitrogen which has been dried, filtered and heated to a temperature of about 120 degrees C., is supplied to the drying column through a line 36. The ultrapure water droplets dry rapidly and completely as they progress through drying column 34. Thus, the drying column output is a particle stream composed of multiple non-volatile residue particles. Every droplet provided to the drying column from the atomizer yields a residue particle. Cleaner ultrapure water produces smaller residue particles.

Non-volatile residue particles leaving the drying column progress through a conduit 38 to a diffusion filter 40, where ultrafine particles (below a predetermined size) are removed from the particle stream. More particularly, the ultrafine particles cling to the walls of filter 40 due to Brownian movement. The remaining particles are provided through a conduit 42 to a condensation particle counter (CPC) 44, sometimes referred to as a condensation nucleus counter.

In condensation particle counter 44, the stream of particles (supported by the air or nitrogen) travels through a chamber saturated with a vapor, e.g. of n-butyl alcohol, after which the stream is cooled sufficiently to supersaturate the vapor. The vapor condenses onto the particles forming aerosol droplets substantially larger than the particles themselves. After condensation, the aerosol droplets travel through a viewing region or volume 46 defined by a laser and associated optics. For further information on this type of device, reference is made to U.S. Pat. No. 4,790,650 (Keady), assigned to the assignee of this application. For a further description of non-volatile residue monitors, reference is made to U.S. Pat. No. 5,098,657 (Blackford et al), also assigned to the assignee of this application, and incorporated by reference herein.

Condensation particle counter 44 detects each aerosol droplet passing through the viewing volume, and thus generates a particle count corresponding to the number of non-volatile residue particles passing through monitor 24. The CPC output is an electrical signal, which is provided to a microprocessor 48. Microprocessor 48 includes an electronically erasable programmable read only memory (EEPROM) 50 in which conversion information is stored. Based on this conversion information, microprocessor 48 generates an output indicating the concentration of non-volatile residue in terms of parts per billion (PPB). The microprocessor output is provided to a video display terminal 52. Display terminal 52 provides a continuously updated record of non-volatile residue concentration in the ultrapure water.

Beyond monitoring the purity of the water, it also is necessary to monitor the purity of various solvents employed in semiconductor device fabrication, e.g. for etching or depositing material during production stages, for cleaning semiconductor wafers between stages, and for measuring residual contaminates extracted from components cleaned with the solvent. Accordingly, a syringe injector 54, precisely controlled by a stepper motor (not shown) is connected to fitting 22 via a conduit or needle 56. To ensure against contamination, T fitting 22 includes a septum which operates to close the opening created by withdrawing the needle after injection. A preferred syringe is available from Becton-Dickinson & Company of Rutherford, N.J., and identified as Model No. 9663. A removable hypodermic needle is used in combination with the syringe. The syringe has a 60 ml capacity, and is controlled by the stepper motor to deliver the test solvent at a preferred rate of about 0.030 ml per minute. Thus, for a deionized ultrapure water delivery rate of 60 ml per minute, the solvent forms only about 0.05 percent of the composite liquid (i.e. the combination of solvent and water). This extreme dilution virtually eliminates any harmful effect the solvent might have upon the system, and enables substantial testing based upon minute quantities of the solvent.

Syringe injector 54 is not operated continuously. Rather, the syringe is actuated intermittently, with each test lasting several minutes. When syringe injector 54 is not actuated, residue monitor 24 receives only the ultrapure water, and monitors water quality in the manner discussed above. When the syringe is actuated, the solvent under test is supplied at the preferred continuous rate, and mingles with the ultrapure water to provide a composite fluid flow to the residue monitor.

At a mixing valve 58 along conduit 26, the solvent and the ultrapure water are thoroughly mixed, to insure that residue monitor 24 receives a homogeneous, uniform mixture. Mixing valve 58 includes a valve ball 60 within an enlarged portion 62 of conduit 26. The arrangement forces both the water and the solvent to flow along the relatively constricted area between valve ball 60 and conduit 26, increasing the fluid velocity and causing turbulent flow just downstream of the valve, as indicated by the arrows to the right of the valve ball as viewed in FIG. 2.

During testing, the residue monitor output is based on residue particles generated as a result of the composite flow. During "normal" operation, only the ultrapure water is provided to residue monitor 24, and the monitor output is based only upon the residue concentration in the water. Accordingly, the residue concentration in the solvent itself is derived in microprocessor 48, by subtracting a background level of residue concentration (in the ultrapure water, alone) from a composite level of concentration (based on the composite fluid including solvent and water). The result is a value representing concentration in the solvent alone, in particles per $cm^3$. This value is converted using EEPROM 50, to yield a value for concentration in parts per billion.

While one preferred rate of solvent injection is 0.03 ml per minute as indicated above, other injection rates may be suited for different solvents and applications. The chart in FIG. 3 illustrates the variance in concentration (PPB), responsive to changes in the rate at which the solvent is injected into the fluid stream. Five different rates of injection are graphically indicated at levels 64, 66, 68, 70 and 72. There is a substantially linear relationship between the injection rate and the resulting solvent residue concentration.

The chart in FIG. 4 illustrates, on a log/log scale, a substantially linear relationship of condensation particle counter output concentration (particles per cm$^3$), and concentration in parts per billion as measured using an atomic absorption spectrometer (AAS), in connection with a potassium chloride solution. The substantially linear relationship verifies the utility of counting particles to determine residue concentration.

FIG. 5 illustrates an alternative embodiment monitoring system 74, in which a pump 76 supplies ultrapure deionized water to a non-volatile residue monitor 78 via a conduit 80, a "T" fitting 82 and a conduit 84. Residue monitor 78 is substantially similar to monitor 24 of system 16, and provides its output to a microprocessor 86 for ultimate display by a video display terminal 88. Microprocessor 86 and display terminal 88 are substantially similar to their counterparts in system 16.

The means of injecting the solvent or other test liquid is a microliter syringe 90, in combination with a hypodermic needle 92. Suitable syringes are available from the Hamilton Company of Reno, Nev., and include a 10 microliter capacity syringe identified as Model No. 801RN, and a 100 microliter capacity syringe identified as Model No. 810RN. Thus, as compared to syringe injector 54 of system 16, syringe 90 is much smaller in capacity, i.e. smaller by about three orders of magnitude.

The solvent is injected into the fluid stream via a conduit 94 to fitting 82, where the solvent is merged into the fluid stream that also includes the ultrapure water. To insure against contamination, fitting 82 includes a septum which operates to close the opening created by withdrawal of the needle after injection.

However, the introduction of the solvent in system 74 differs from that in system 16 in several respects. First, the amount of solvent injected, even at full capacity of a 100 ml syringe, is substantially less than the amount of solvent injected in system 16 by several orders of magnitude. Secondly, the solvent in syringe 90 is injected substantially instantaneously, each injection lasting only a fraction of a second. Thus there is no need to maintain a constant injection rate over time. Finally, system 74 does not incorporate a mixing valve, or any other structure to introduce turbulent flow in the fluid stream. Instead, the fluid flow is essentially laminar.

Figure 6:
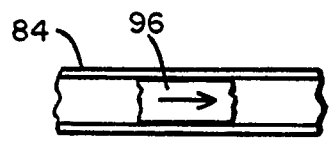
FIG. 6 is an enlarged partial view of FIG. 5.

As a result of the essentially laminar flow, each solvent injection forms a plug, as illustrated at 96 in FIG. 6. Solvent plug 96 flows in the fluid stream with the ultrapure water at the same linear velocity as the ultrapure water, yet remains separate and distinct. In practice, this phenomenon can be observed when conduit 84 is constructed of a transparent material. Plugs of solvent are visible, due to the fact that the solvent and water have different indices of refraction.

The maintenance of laminar flow to preserve the integrity of the solvent plugs is a key factor in residue measuring efficiency. To this end, conduit 84 is much smaller than its counterpart in system 16. More particularly, the outside diameter of conduit 84 is about one sixteenth of an inch in diameter. Conduit 26 of system 16 has an outside diameter of about one quarter inch. Given the flow rate (of ultrapure water) of from 50 to 70 ml in both systems, it is to be appreciated that linear velocity of the fluid, as it flows toward the atomizer, is substantially greater in system 74. To further insure against unwanted mixing of the solvent and water, the length of conduit 84, and the total flow path from fitting 82 to the atomizer, is as short as practicable, e.g. a few inches.

The instantaneous burst injection of the solvent, the increased linear fluid flow velocity, and the shorter path to the atomizer, contribute to substantially reducing the time involved in testing the solvent. Test results are displayed on terminal 88 within a matter of seconds after injection of a solvent burst, permitting several repetitions of the test to verify the accuracy of results, and providing essentially "real time" non-volatile residue concentration readings, substantially increasing the probability that timely corrective action may be taken in response to results that exceed an acceptable maximum concentration.

Figure 7:
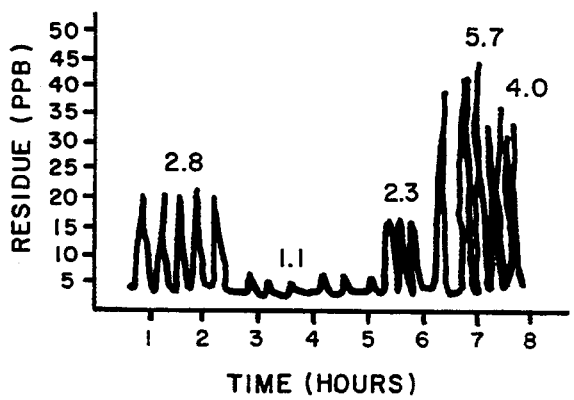
FIG. 7 is a chart illustrating non-volatile residue concentration data taken over a designated time of operating the system of FIG. 5.
Figure 8:
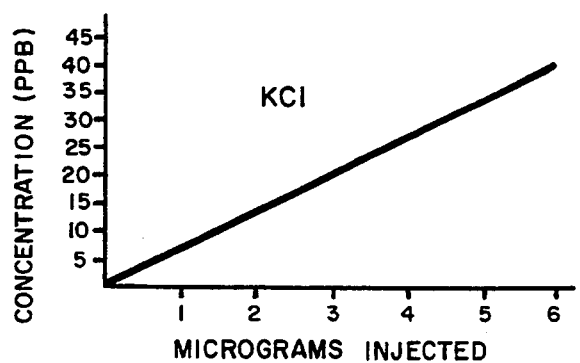
FIG. 8 is a conversion chart relating residue concentration to micrograms of solvent injected, in the system of FIG. 5.

FIG. 7 is a plot of residue concentration (PPB) over time, based upon a potassium chloride (KCl) solution. The solvent plugs cause sharp peaks as shown. Depending upon the software utilized in microprocessor 86, either the peak heights or (more preferably) the areas beneath the peaks can be used to compute non-volatile residue concentrations. The numbers shown directly above the peaks, ranging from 1.1 to 5.7, are the micrograms per injection of the KCl solution. Thus, the higher peaks correspond to increased levels of the solution in the corresponding injections. The relationship of residue concentration plotted against the amount of solution injected is substantially linear, as illustrated in FIG. 8.

In practice, it has been found preferable to employ water-soluble solvents in a system utilizing ultrapure water as the carrier liquid. Water soluble solvents were found to flow smoothly through the conduit toward the atomizer. Water insoluble fluids, by contrast, tended to break up into droplets that occasionally adhered to the walls of the conduit, reducing the efficiency of the residue monitor. To minimize or eliminate this problem, liquids other than water may be employed as carrier liquids. For example, system 74 can be employed to detect non-volatile residue in skin oil, with ethanol as the carrier liquid.

Figure 9:
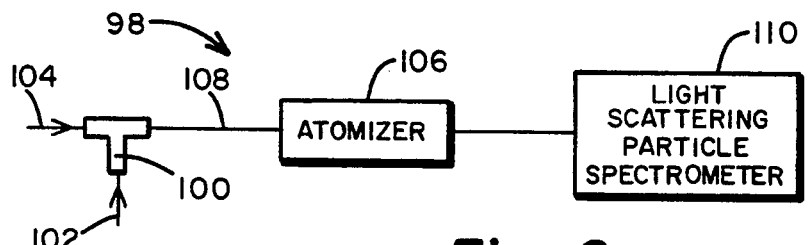
FIGS. 9–12 are schematic illustrations of further alternative systems for determining non-volatile residue concentrations, constructed according to the present invention.

FIG. 9 illustrates part of an alternative system 98 in which ultrapure water is supplied to a T fitting 100 via a conduit 102, and a solvent is supplied to the fitting via a conduit 104. The composite liquid flows to an atomizer 106 through a conduit 108. The droplet output of atomizer 106 is supplied to a light scattering particle spectrometer 110. For further information regarding a light scattering particle spectrometer, reference is made to U.S. Pat. No. 4,794,086 (Kasper et al). The output of spectrometer 110 is provided to a microprocessor and a video display terminal (not shown).

Figure 10:
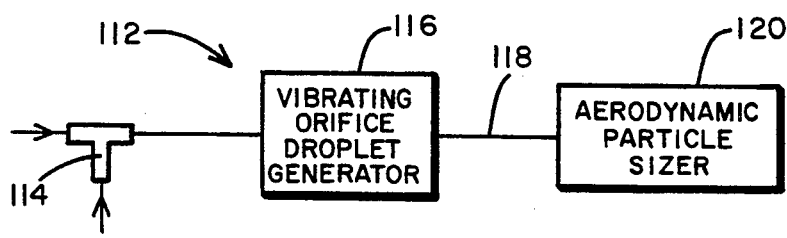

A further alternative system 112 is shown in FIG. 10, where ultrapure water and a solvent are provided to a T fitting 114, and the composite liquid provided to a vibrating orifice droplet generator 116 via a conduit 118. The output of droplet generator 116 is a series of aerosol droplets of a precisely determined size. The droplets are provided to an aerodynamic particle sizer 120. The output of particle sizer 120 is provided to a microprocessor and a video display terminal. For further information regarding a vibrating orifice droplet generator and an aerodynamic particle sizer, reference is made to the aforementioned U.S. Pat. No. 4,794,086.

Figure 11:
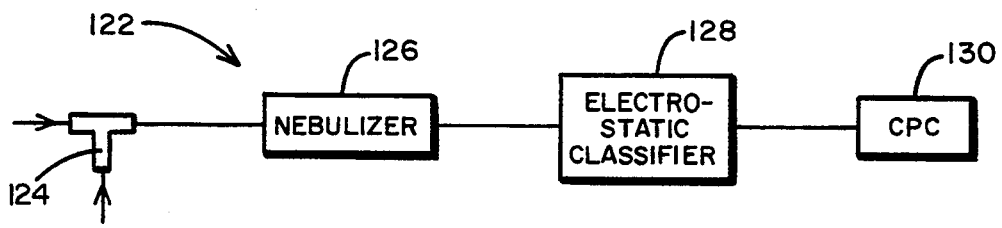

FIG. 11 illustrates a further alternative system 122 in which a T fitting 124 provides a composite liquid flow of ultrapure water and a solvent to a nebulizer 126. The output of nebulizer 126 is provided to an electrostatic classifier 128, with the output of the electrostatic classifier being provided to a condensation particle counter 130.

Figure 12:
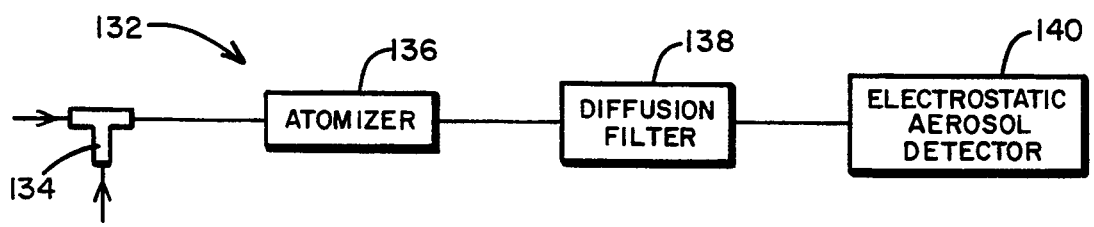

FIG. 12 illustrates yet another system 132 in which the combined solvent/ultrapure water output of a T fitting 134 is provided to an atomizer 136. The droplet output of the atomizer proceeds through a diffusion filter 138 to electrostatic aerosol detector 140. As indicated in the aforementioned U.S. Pat. No. 5,098,657, an electrostatic aerosol detector can be employed in lieu of a condensation particle counter.

Thus, in accordance with the present invention, a simple, low cost and reliable system achieves accurate readings of non-volatile residue concentrations in solvents, requiring only minute quantities of the solvents for testing. Potential hazards from handling large amounts of the solvents, undesirable emissions to the atmosphere, and solvent disposal problems are all significantly reduced. Tests can be performed rapidly and repeatedly, and provide substantially real time results, particularly when the solvent is injected instantaneously in the form of solvent bursts. The testing systems can employ ultrapure water as a carrying liquid for the solvent. This facilitates testing of solvents, largely with equipment already utilized in connection with the ultrapure water systems, as modified to accommodate solvent injection.

What is claimed is:

1. An apparatus for monitoring the concentration of non-volatile residue in a test liquid, including:
   a droplet forming means for receiving a fluid stream and for generating multiple liquid droplets comprised of at least a portion of the fluid stream;
   a first fluid supply means in fluid communication with the droplet forming means for providing a carrier liquid stream of a carrier liquid, at a substantially constant first flow rate;
   a second fluid supply means in fluid communication with the first fluid supply means, for introducing a test liquid into the carrier liquid stream at a selected point upstream of the droplet forming means, said test liquid being introduced controllably and intermittently whereby said fluid stream, downstream of the selected point, includes a first fluid stream portion that includes the test liquid corresponding to actuation of the second fluid supply means, and a second fluid stream portion that does not include the test liquid corresponding to an inactive state of the second fluid supply means;
   a drying means disposed downstream of the droplet forming means for causing evaporation of the liquid droplets to form a particle stream of multiple substantially non-volatile residue particles; and
   a particle counting means disposed downstream of the drying means to receive the particle stream, said particle counting means including a particle sensing region, and generating first particle count based on the substantially non-volatile residue particles generated as a result of the first fluid stream portion and passing the sensing region and a second particle count based on the substantially non-volatile residue particles generated as a result of the second fluid stream portion and passing through the sensing region.

2. The apparatus of claim 1 further including:
   an information processing means operatively coupled to the counting means, for receiving the first and second particle counts and, based upon the particle counts, generating an indication of the concentration of non-volatile residue in the test liquid.

3. The apparatus of claim 2 wherein:

the information processing means is a microprocessor including an electrically erasable programmable read only memory for converting the first and second particle counts to a representation of said concentration in parts per billion.

4. The apparatus of claim 1 wherein:

said second fluid supply means comprises a motor controlled syringe injector which, when actuated, introduces the test liquid at a substantially constant second flow rate.

5. The apparatus of claim 4 wherein:

the second fluid supply means is constructed and arranged to introduce the test liquid at the second flow rate is less than one percent of the first flow rate.

6. The apparatus of claim 5 further including:

a mixing valve downstream of said selected point and upstream of the droplet forming means, for causing a turbulent flow in the fluid stream to combine the carrier liquid and the test liquid into a substantially uniform mixture.

7. The apparatus of claim 1 wherein:

the second fluid supply means comprises a syringe.

8. The apparatus of claim 1 wherein:

the second fluid supply means introduces the test liquid in substantially instantaneous bursts, each of the bursts being substantially non-turbulent to form a plug of the test liquid flowing in the fluid stream with the carrier liquid, yet remaining separate and distinct from the carrier liquid.

9. The apparatus of claim 8 wherein:

the first fluid supply means is constructed and arranged to supply the carrier liquid at the first flow rate at least 50 milliliters per minute, the duration of each of said bursts is at most 0.5 seconds, and the amount of the test liquid introduced in each of the bursts is at most one milliliter.

10. The apparatus of claim 9 wherein:

the second fluid supply means introduces the test liquid in the form of a solvent soluble in the carrier liquid.

11. The apparatus of claim 10 wherein:

the first fluid supply means supplies the carrier liquid in the form of ultrapure, deionized water.

12. The apparatus of claim 6 wherein:

the second fluid supply means introduces the test liquid in the form of a solvent miscible in the carrier liquid.

13. The apparatus of claim 12 wherein:

the first fluid supply means supplies the carrier liquid in the form of ultrapure, deionized water.

14. The apparatus of claim 1 wherein:

said droplet forming means comprises one selected of from the group of an atomizer, a nebulizer, and a vibrating orifice droplet generator.

15. The apparatus of claim 1 wherein:

said particle counting means comprises one selected from the group of a condensation particle counter, a light scattering particle spectrometer, an aerodynamic particle sizer, and an electrostatic aerosol detector.

16. The apparatus of claim 1 wherein:

the particle counting means comprises a condensation particle counter in combination with a component upstream of the condensation particle counter, said component being selected from the group of: a diffusion filter, and an electrostatic classifier.

17. A process for determining the concentration of non-volatile residue in a test liquid, including the steps of:

moving a carrier liquid in a fluid stream at a substantially constant first flow rate;

controllably and intermittently introducing a test liquid into the fluid stream at a selected point along the fluid stream whereby the fluid stream, downstream of the selected point, includes a first fluid stream portion including the test liquid and a second fluid stream portion that does not include the test liquid;

downstream of the selected point at which the test liquid is introduced, generating multiple liquid droplets comprised of at least a portion of the fluid stream;

drying the liquid droplets to form a particle stream of multiple substantially non-volatile residue particles;

counting at least a predetermined portion of the non-volatile residue particles in the particle stream, to obtain a first particle count based on the substantially non-volatile residue particles generated as a result of the first fluid stream portion and a second particle count based on the substantially non-volatile residue particles generated as a result of the second fluid stream portion; and deriving the concentration of non-volatile residue in the test liquid, based upon the first and second particle counts.

18. The process of claim 17 wherein:
the test liquid is introduced into the fluid stream at a substantially constant second flow rate.

19. The process of claim 18 wherein:
said second flow rate is at most one percent of said first flow rate.

20. The process of claim 19, wherein:
the test liquid is miscible in the carrier liquid, and the step of introducing the test liquid includes causing a turbulent flow in the fluid stream to thoroughly mix the test liquid and the carrier liquid.

21. The process of claim 20 wherein:
said second particle count comprises a background count corresponding to only the carrier liquid in the fluid stream, and the first particle count comprises a composite particle count corresponding to a mixture of the test liquid and carrier liquid in the fluid stream; and
wherein the step of deriving the concentration includes subtracting the background count from the composite count.

22. The process of claim 17 wherein:
the test liquid is introduced in substantially instantaneous bursts.

23. The process of claim 22 wherein:
each burst of the test liquid is introduced in a substantially non-turbulent manner to form a plug of the test liquid flowing in the fluid stream with the carrier liquid, and remaining separate from the carrier liquid.

24. The process of claim 23 wherein:
the volume of the test liquid in each burst is less than the volume of the carrier liquid flowing past a given point in the fluid stream each second, and wherein the burst is introduced into the fluid stream in substantially less than one second.

25. The process of claim 17 including the further step of:

after said drying step, saturating the particle stream with a liquid vapor, and then cooling the particle and vapor stream below the supersaturation point of the vapor to cause the vapor to condense on the residue particles, to form aerosol liquid droplets; and wherein the counting step comprises counting at least a predetermined portion of the aerosol liquid droplets.

26. The process of claim 25 including the further step of:

after said drying step and prior to said saturating step, removing a selected portion of the non-volatile residue particles from the particle stream, based upon the size of the particles in the selected portion.

27. A process for determining the concentration of non-volatile residue in a test liquid, including the steps of:

moving a carrier liquid in a fluid stream at a substantially constant first flow rate;

controllably and intermittently introducing a test liquid, in the form of at least several instantaneous bursts, into the fluid stream at a selected point along the fluid stream, whereby the fluid stream downstream of the selected point includes bursts of the test liquid, and regions of the carrier liquid separated from one another by the bursts;

downstream of the selected point, generating multiple liquid droplets comprised of at least a portion of the fluid stream;

drying the liquid droplets to form a continuous particle stream of multiple substantially non-volatile residue particles; counting at least a predetermined portion of the non-volatile residue particles in the particle stream, to obtain a first particle count based on the substantially non-volatile particles generated as a result of the carrier liquid and a second particle count based on the substantially non-volatile particles generated as a result of the bursts; and deriving the concentration of non-volatile residue in the test liquid, based upon the first and second particle count.

28. The process of claim 27 wherein:
the volume of the test liquid in each burst is less than the volume of the carrier liquid flowing past a given point in the fluid stream each second, and wherein each burst is introduced into the fluid stream in substantially less than one second.

* * * * *